United States Patent [19]

Koch

[11] 3,954,743
[45] May 4, 1976

[54] COUMARIN AND COUMARINIMIDE DERIVATIVES

[75] Inventor: Werner Koch, Oberwil, Switzerland

[73] Assignee: Sandoz Ltd., Basel, Switzerland

[22] Filed: July 9, 1973

[21] Appl. No.: 377,537

[30] Foreign Application Priority Data
July 11, 1972  Switzerland.................. 10355/72
Dec. 15, 1972  Switzerland.................. 18303/72

[52] U.S. Cl. ............................. 260/243 D; 8/1 W; 8/179; 8/178 R; 8/162 R
[51] Int. Cl.² ................................ C07D 285/24
[58] Field of Search ......................... 260/243

[56] References Cited
UNITED STATES PATENTS
| | | | |
|---|---|---|---|
| 3,644,348 | 2/1972 | Irikura et al. | 260/243 D |
| 3,691,162 | 9/1972 | Yale | 260/243 D |
| 3,793,318 | 2/1974 | Lafon | 260/243 D |

FOREIGN PATENTS OR APPLICATIONS
| | | |
|---|---|---|
| 372,307 | 11/1963 | Switzerland |
| 465,551 | 1/1969 | Switzerland |

Primary Examiner—Joseph A. Narcavage
Assistant Examiner—Jose Tovar
Attorney, Agent, or Firm—Gerald D. Sharkin; Richard E. Vila; Joseph J. Borovian

[57] ABSTRACT

Compounds of the formula

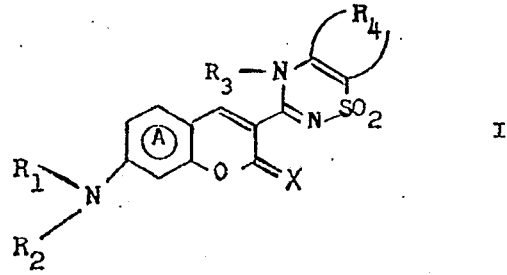

in which
X signifies oxygen or =NH,
$R_1$ signifies an alkyl, alkenyl or phenyl radical which is unsubstituted or substituted,
$R_2$ signifies hydrogen or one of the meanings of $R_1$, or $R_1$ and $R_2$ together with the vicinal nitrogen atom form a heterocyclic ring system,
$R_3$ signifies hydrogen, acyl or an alkyl or phenyl radical which is unsubstituted or substituted, and
$R_4$ signifies the atoms needed to complete an aromatic carbocyclic or heterocyclic ring system,
and the ring A and chain $R_4$ are unsubstituted or substituted,
are useful fluorescent dispersion dyestuffs.

10 Claims, No Drawings

COUMARIN AND COUMARINIMIDE DERIVATIVES

IMPROVEMENTS IN OR RELATING TO ORGANIC COMPOUNDS

The present invention relates to new coumarin and coumarinimide derivatives, which are fluorescent dispersion dyestuffs.

The invention provides a compound, free of carboxyl and sulphonic acid groups, of formula I,

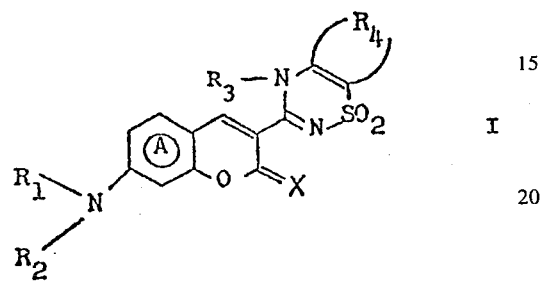

in which
X signifies oxygen or =NH,
$R_1$ signifies an alkyl, alkenyl or phenyl radical which is unsubstituted or substituted,
$R_2$ signifies hydrogen or one of the meanings of $R_1$, or
$R_1$ and $R_2$ together with the vicinal nitrogen atom form a heterocyclic ring system,
$R_3$ signifies hydrogen, acyl or an alkyl or phenyl radical which is unsubstituted or substituted, and
$R_4$ signifies the atoms needed to complete an aromatic carbocyclic or heterocyclic ring system,
and the ring A and chain $R_4$ are unsubstituted or substituted.

Any alkyl or alkenyl groups in the molecule may be straight-chain or branched, and contain 1 to 7 carbon atoms, the alkyl groups preferentially 1, 2, 3 or 4 carbon atoms. The alkyl groups may also be cyclic; cyclohexyl or methylcyclohexyl groups are preferred cycloalkyl radicals.

Suitable substituents for the substituents on formula I include, for example, one or more halogen atoms (in particular chlorine and bromine atoms), alkoxy, hydroxy, cyano, thiocyano, vinyl, amino, alkylamino, dialkylamino, phenylamino, N-phenyl-N-alkylaminio, phenyl, phenoxy, acyl, acyloxy or acylamino groups. Specially preferred on account of price are unsubstituted methyl or ethyl groups.

Any phenyl groups in the molecule and also the nuclei designated A and $R_4$ may carry the substituents named above, or an alkyl, trifluoromethyl or nitro group.

If $R_1$ and $R_2$ together with the nitrogen atoms linked with them constitute a heterocyclic ring system, this generally means a 5- or 6-membered ring which, as described above, may carry substituents, and which may contain in addition to the =CH or —$CH_2$ groups, other heteroatoms — in particular oxygen, sulphur or nitrogen atoms — and may be saturated or unsaturated.

$R_4$ completes a benzene ring preferentially, though it may also complete a pyridine, pyrimidine, pyrryl, pyrazolyl or imidazolyl ring. These groups may have other rings attached, yielding, for example, naphthalene, quinoline or indole structures.

Preferred acyl groups are of the formula R—Y— or R'—Z—, in which R denotes a hydrocarbon radical which may carry the substituents mentioned above and/or contain heteroatoms, preferentially an alkyl or phenyl radical which may be substituted,
Y is a radical —O—CO—, —$SO_2$— or —O—$SO_2$—,
R' is a hydrogen atom or R,
Z is a radical —CO—, —NR''CO— or —NR''$SO_2$—
R'' is a hydrogen atom or R.

Of particular interest are compounds of formula Ia,

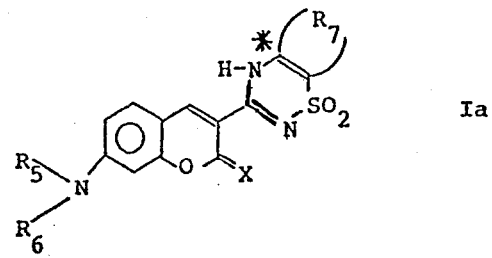

in which
X signifies oxygen or =NH,
$R_5$ signifies alkyl which is unsubstituted or substituted by hydroxyl, alkoxy, cyano, formyloxy, alkylcarbonyloxy, alkoxycarbonyloxy, alkoxycarbonyl or benzoyloxy as substituents, allyl or phenyl,
$R_6$ signifies hydrogen or one of the meanings of $R_5$,
$R_7$ signifies a radical of the formula:

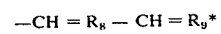

in which $R_8$ and $R_9$ independently signify =CH— or =N— which is unsubstituted or substituted by chlorine, bromine, methyl, alkoxy, cyano, thiocyano, trifluoromethyl, alkoxycarbonyl, benzyloxycarbonyl, alkylcarbonyloxy, acetylamino, propionylamino, benzoylamino, aminosulphonyl, alkylaminosulphonyl, dialkylaminosulphonyl, phenylaminosulphonyl or N-alkyl-N-phenylaminosulphonyl, or a radical of the formula:

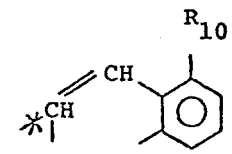

in which
$R_{10}$ signifies aminosulphonyl, alkylaminosulphonyl or dialkylaminosulphonyl, and
the end denoted with * is linked to the carbon atom marked similarly in formula Ia, and
the alkyl and alkoxy groups named contain 1 to 4 carbon atoms.

More preferred compounds are those of formula Ib,

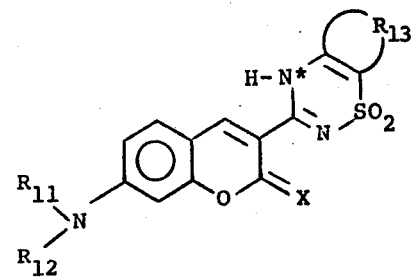

in which $R_{11}$ signifies ethyl, which is unsubstituted or substituted by cyano, acetoxy, propionyloxy, methoxycarbonyl, ethoxycarbonyl, methoxycarbonyloxy or ethoxycarbonyloxy, $R_{12}$ signifies allyl, phenyl or one of the meanings of $R_{11}$, $R_{13}$ signifies a radical of the formula:

$$-CH = R_8 - CH = CH-*,$$

which is unsubstituted or substituted by chlorine, bromine, methyl, methoxy, ethoxy, cyano, thiocyano, trifluoromethyl, methoxycarbonyl, ethoxycarbonyl, aminosulphonyl, methylaminosulphonyl or dimethylaminosulphonyl, with the end denoted * linked to the carbon atom marked similarly in formula Ib, and $R_8$ denotes $=CH-$ or $=N-$.

Specially preferred compounds are those of formula Ic,

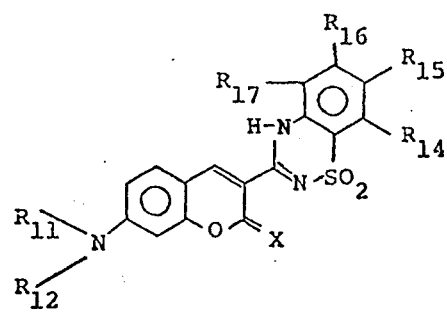

Ic in which $R_{11}$, $R_{12}$ and X are as defined above, $R_{14}$ and $R_{16}$ each independently signify hydrogen, chlorine, bromine, methyl, methoxy, cyano or trifluoromethyl, $R_{15}$ signifies methoxycarbonyl, ethoxycarbonyl or one of the significances given above for $R_{14}/R_{16}$, and $R_{17}$ signifies aminosulphonyl, methylaminosulphonyl, dimethylaminosulphonyl or one of the meanings given under $R_{14}/R_{16}$.

The invention also provides a process for producing compounds of formula I, comprising a. condensing a compound of formula II,

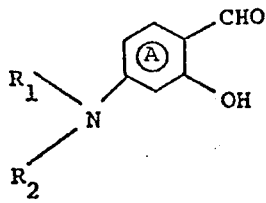

II in which $R_1$, $R_2$ and A are as defined above, with a compound of formula III,

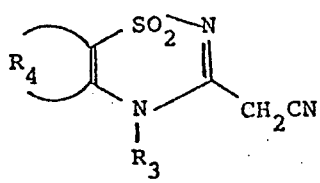

III in which $R_3$ and $R_4$ are as defined above, to form a compound of formula I',

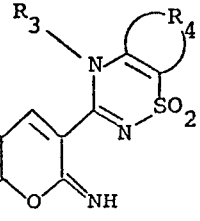

I' in which $R_1$ to $R_4$ and A are as defined above, or b. hydrolysing a compound of formula I' and splitting off ammonia, to form a compound of formula I'',

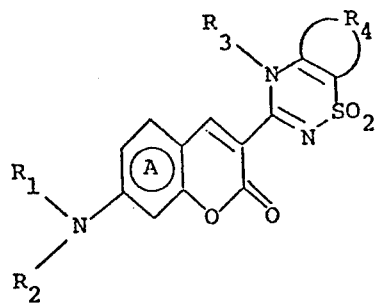

I'' in which $R_1$ to $R_4$ and A are as defined above.

The condensation of the aldehyde of formula II with the compound of formula III in process variant (a), is suitably effected in an inert, preferably anhydrous solvent, such as ethanol, methanol, dimethylformamide, dimethylsulphoxide or dioxane. The reaction is preferably carried out in the presence of an organic base such as piperidine, pyrrolidine or pyridine, and is suitably effected at temperatures from 30° to 180°C, preferably at the boiling point of the solvent in question, under reflux. Where an alcohol is used as solvent, the coumarinimides occur as an insoluble product during the course of the reaction. The compounds of formula I' are usually obtained in a very pure state and with excellent yields, and may be isolated in conventional manner, for example, by concentration and filtering-off.

In process variant (b), hydrolysis of the compound of formula I' may be accomplished in conventional manner, such as by boiling in organic acids (e.g. acetic acid) or diluted mineral acids (1 to 10% hydrochloric acid). Here it may be of advantage to add a water-soluble organic solvent (such as methanol or ethanol) to the dilute mineral acid. It is believed that the ring substituted by the imine group is cracked by hydrolysis, then splitting off ammonia causes ring closure. The separation of ammonia and with it the ring closure to the coumarin compound of formula I'' occur practically simultaneously, under the preferred reaction conditions.

The compounds of formula III are new and may, for example, be obtained by the condensation of a compound of formula IV,

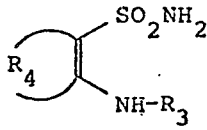

IV in which $R_3$ and $R_4$ are as defined above, with cyanoacetic acid, cyanoacetic alkyl ester (alkyl of 1 to 4 carbon atoms) or cyanoacetic chloride. The reactants are preferably used in approximately equivalent amounts. The reaction is preferably effected in a polar solvent of high boiling point (e.g. dimethylformamide), and preferably at temperatures from 140° to 200°C, more preferably at about 160°C. It is preferred to use an acid-binding medium such as piperidine or sodium carbonate. The reaction lasts 5 to 10 hours under preferred conditions. Isolation of the product may be achieved, for example, by pouring on water, in which the compound of formula III has only very poor solubility. The reaction solution may also be cooled down to about 90° – 100°C and water added until there is a slight turbidity, after which cooling is continued, and the compound of formula III crystallizes out in very pure form.

Those compounds whose preparation is not specifically described may be prepared by methods known in the literature or methods analogous to known methods or to methods described herein, from known starting materials.

The compounds of formula I may be processed into dyeing preparations in a generally familiar manner, e.g. by milling in the presence of dispersing agents and/or fillers. With the dried preparations, which are possibly dried by atomization or under vacuum, after adding more or less water it is possible to dye, pad or print, with a so-called long or short liquor. The dyestuffs are usually absorbed excellently from the aqueous suspension formed onto textile materials of synthetic or semi-synthetic, hydrophobic organic substances of high molecular weight. They are particularly indicated for dyeing or printing textiles of linear, aromatic polyesters, as well as those of cellulose-2½-acetate, cellulose triacetate and polyamide synthetics. Dyeing or printing is done by conventional techniques, such as that described in French Pat. No. 1,445,371.

The dyeings obtained generally have good fastnesses, particularly to light, thermosetting, sublimation and pleating. They have also generally good wet-fastness, e.g. against water, sea water, washing and perspiration, and fastness to solvents, in particular dry cleaning fluids, to textile lubricants, to rubbing, to cross-dyeing, to ozone, to flue gas and to chlorine. They are generally resistant to the action of the various permanent press processes and the so-called soil-release finishes. The reduction resistance (when dyeing wool) and the resist with wool and cotton are also usually good.

The new compounds according to the invention may also, especially after the processing or conditioning usual with pigment dyestuffs, be suitable for, say, dyeing bulk plastics, including plastics or synthetic resins containing solvents or free of these (in paints with oil or water base, in lacquers of various kinds, for spin-dyeing viscose, polyacrylonitrile, aromatic polyesters or cellulose acetate, for pigmenting polyethylene, polypropylene, polystyrene, polyvinyl chloride, rubber and artificial leather). They may also be suitable for inks used by the printing industry, for pulp dyeing, for coating textiles or for pigment printing.

The dyeings obtained are usually light- and migration-fast. They distribute well in plastics, stand up well to solvents and painting over, and have good transparency.

The very frequently observed phenomenon of mixtures of dyestuffs excelling single dyestuff components in affinity can be observed in this case too. Hence the cheaper compounds of formula I, not substituted in the nucleus $R_4$ or substituted in simple fashion, may be used advantageously as mixtures.

In the Examples that follow, the parts are parts by weight and the percentages are weight percentages. The temperatures are given in degrees Centigrade.

EXAMPLE 1 a. 33.15 parts 3-cyanomethyl-1,2,4-benzothiadiazine-1,1-dioxide and 28.95 parts 4-N-diethylamino-2-hydroxybenzaldehyde are dissolved in 300 parts ethanol and after adding 5 parts piperidine heated quickly to boiling point. The deep yellow reaction product forms almost at once with almost 100% yield and is precipitated. After cooling it is filtered and dried. A recrystallized sample from dimethylformamide had a melting point of 282°–283° (uncorr.).

Elementary analysis

|  | C | H | N | S |
|---|---|---|---|---|
| Found: | 60.4 % | 5.1 % | 13.7 % | 8.1 % |
| Calculated: | 60.6 % | 5.1 % | 14.1 % | 8.1 % |

The mass spectrum (m/e=396), the 100 MHz proton resonance spectrum and the IR data are valid for the empirical formula $C_{20}H_{20}N_4O_3S$ and the following structure:

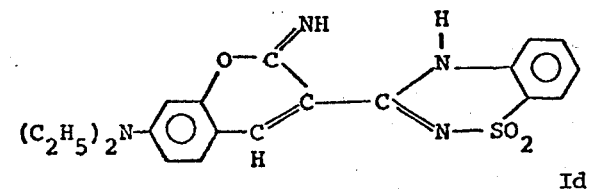

Id

The electron spectrum (in dimethyl sulphoxide) is:

$\lambda = 280.5$ m$\mu$     (log $\epsilon$ = 4.04)
$\lambda_{max} = 462$ m$\mu$     (log $\epsilon$ = 4.70)

b. To produce the corresponding coumarin compound, 56.7 parts of the compound produced above in (a), are suspended in a mixture of 300 parts ethanol and 200 parts hydrochloric acid (5%) and boiled vigorously for four hours under reflux. The ring cleavage and reclosure take place with virtually 100% yield. After cooling the product is filtered, washed free of acid and dried. Without further treatment it can be made up into a dispersed dyestuff. As such it will dye polyester fibre materials to brilliant yellow shades with strong greenish fluorescence, characterized by excellent fastness properties.

A sample of dyestuff obtained in accordance with the above procedure b), recrystallized twice from dimethylformamide, had a boiling point of 320°–321° (uncorr.).

Elementary analysis

|  | C | H | N | S |
|---|---|---|---|---|
| Found: | 60.5 % | 4.9 % | 10.7 % | 8.2 % |
| Calculated: | 60.4 % | 4.8 % | 10.6 % | 8.1 % |

The mass spectrum (m/e = 397), the 100 MHz proton resonance spectrum and the IR data correspond to the empirical formula $C_{20}H_{19}N_3O_4S$ and the following structure:

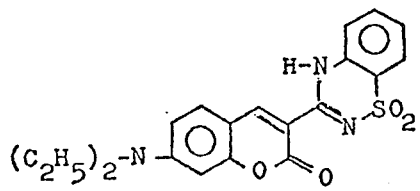

The electron spectrum (in dimethyl sulphoxide) is:

| | |
|---|---|
| $\lambda_1 = 280$ m$\mu$ | (log $\epsilon = 4.01$) |
| $\lambda_{max} = 456$ m$\mu$ | (log $\epsilon = 4.76$) |

Fluorescence spectrum in dimethylformamide:

| | |
|---|---|
| Excitation maximum: | 456 m$\mu$ |
| Emission band: | 498 m$\mu$ |
| In dioxane: | |
| Excitation maximum: | 440 m$\mu$ |
| Emission band: | 472 m$\mu$ | c. The starting material 3-cyanomethyl-1,2,4-benzothiadiazine-1,1-dioxide is prepared as follows:

61 parts 1-aminobenzene-2-sulphonamide (produced according to the instructions of Helv. 12, 667 ff, (1929) by sulphonation of 1-chloro-2-nitrobenzene with sodium sulphide, oxychlorination of the resulting 2,2'-dinitrodiphenyl bisulphide-1,1' to 1-nitrobenzene-2-sulphochloride, amidation with ammonia to the corresponding sulphonamide and reduction of the nitro group to the amino group) and 47 parts of cyanoacetic ethyl ester are held for 5 hours at 160° in 170 parts dimethyl acetamide. Ethanol and water separating during the reaction are remove by distillation. After this the reaction mixture is cooled to about 100° and hot water is added to it until a slight turbidity appears. With further cooling the reaction product is precipitated. After filtration and drying a solid product is obtained, which after recrystallization from dimethylformamide has a melting point of 200°.

The product was analyzed and gave the following values:

molecular weight 221 (measured by mass spectrography),
Elementary analysis:

| | C | H | N | S | |
|---|---|---|---|---|---|
| ($C_9H_7N_3O_2S$) | 48.7 | 3.2 | 19.0 | 14.8 | Found |
| | 48.8 | 3.17 | 19.0 | 14.5 | Calculated |

NMR spectrum at 60 MHz (in deuterated dimethyl sulphoxide):

| | | |
|---|---|---|
| Methylene: | 4.25 | PPM $\equiv$ 2 H (singlet) |
| Aromatic hydrogens: | 7.2 – 7.95 | PPM = 4 H (multiplet) | from which the following structural formula can be deduced:

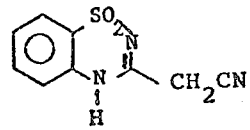

(3-cyanomethyl-1,2,4-benzothiadiazine-1,1-dioxide).

For the dyestuffs in the table following, the substituents are given in accordance with formula Ia. These dyestuffs are produced according to the procedure in Example 1, and their structure and properties established according to the method described previously.

The linkage point on the chain designated $R_7$ is again marked with * where necessary. Dyed onto polyester fibre material, all dyestuffs give yellow dyeings fluorescing with a strong greenish tint. Each example represents two dyestuffs, one in which the X symbol denotes oxygen and one in which the X signifies an imino group; the two dyestuffs are very similar in their properties.

TABLE

| Exple. No. | $R_5$ | $R_6$ | $R_7$ |
|---|---|---|---|
| 2 | —$CH_2CH_2CN$ | —$CH_2CH_2OCOCH_3$ | —CH=CH—CH=CH— |
| 3 | —$CH_2CH_2CH_2CH_3$ | —$CH_2CH_2CH_2CH_3$ | do. |
| 4 | —$CH_2CH_2OH$ | —$CH_2CH_2CN$ | do. |
| 5 | —$CH_2CH_2OCHO$ | —$CH_2CH_2OCHO$ | do. |
| 6 | —$CH_2CH_2COOCH_3$ | —$CH_3$ | do. |
| 7 | —$CH_2CH_2OCOC_2H_5$ | —$CH_2CH_2OCOC_2H_5$ | do. |
| 8 | —$CH_2CH_2OCOOCH_3$ | —$CH_2CH_2OCOOCH_3$ | do. |
| 9 | —$CH_2CH_2OCOOC_2H_5$ | —$CH_2CH_2OCOOC_2H_5$ | do. |
| 10 | —$CH_2CH_2COOC_4H_9$ | —$CH_2CH_2CH_2CH_3$ | do. |
| 11 | —$CH_2CH(CH_3)OCOCH_3$ | —$CH_2CH(CH_3)OCOCH_3$ | do. |
| 12 | —$CH_2CH_2CH_3$ | —$CH_2CH_2CH_3$ | do. |
| 13 | —$CH_2CH_2OCOOCH_2CH_2CH_3$ | —$CH_3$ | do. |
| 14 | —$CH_2CH_2CH_2CH_3$ | —$CH_2CH_2COOCH(CH_3)_2$ | —CH=CH—CH=CH— |
| 15 | —$CH_2CH_2CN$ | —$CH_2CH_2CN$ | do. |
| 16 | —$C_2H_5$ | —$C_2H_5$ | do. |
| 17 | —$CH_2CH_2OC_2H_5$ | —$CH_2CH_2OC_2H_5$ | do. |
| 18 | —$CH_2CH_2OCOC_6H_5$ | —$C_2H_5$ | do. |
| 19 | —$CH_2$—CH=$CH_2$ | do. | do. |
| 20 | —$CH_2CH_2CN$ | H | —CH=C($NHCOC_2H_5$)—CH=CH— |
| 21 | —$CH_2CH_2OCOCH_3$ | H | —CH=C($NHCOC_6H_5$)—CH=CH— |
| 22 | —$C_2H_5$ | —$C_2H_5$ | —CH=C($OCH_3$)—C($OCH_3$)=CH— |
| 23 | do. | do. | *—CH=C(SCN)—CH=CH— |
| 24 | do. | do. | —CH=C(Cl)— C(Cl)=CH— |
| 25 | do. | do. | —CH=C(Br)—C(Br)=CH— |
| 26 | do. | do. | *—CH=C(Cl)—CH=CH— |
| 27 | do. | do. | *—CH—C($CF_3$)—CH=CH— |
| 28 | —$C_2H_5$ | —$C_2H_5$ | *—CH=C(Cl)—CH=C(Cl)— |
| 29 | do. | do. | *—CH=C(Cl)—C($CH_3$)=CH— |

TABLE – Continued

| Exple. No. | $R_5$ | $R_6$ | $R_7$ |
|---|---|---|---|
| 30 | do. | do. | *—C(CH$_3$)=CH—CH=CH— |
| 31 | do. | do. | *—C(Cl)=C(Cl)—C(Cl)=C(Cl)— |
| 32 | do. | do. | *—CH=C(CN)—CH=CH— |
| 33 | do. | do. | *—CH=CH—C(COOCH$_3$)=CH— |
| 34 | do. | do. | *—CH=CH—C(COOC$_2$H$_5$)=CH— |
| 35 | do. | do. | *—CH=CH—C(OCOCH$_3$)=CH— |
| 36 | do. | do. | *—CH=CH—C(OCOC$_2$H$_5$)=CH— |
| 37 | do. | do. | *—CH=CH—C(COOCH$_2$CH$_2$CH$_2$CH$_3$)=CH— |
| 38 | do. | do. | *—CH=CH—C(COOCH$_2$C$_6$H$_5$)=CH— |
| 39 | do. | do. | *—CH=C(NHCOCH$_3$)—CH=CH— |
| 40 | do. | do. | *—C(SO$_2$NH$_2$)=CH—CH=CH— |
| 41 | do. | do. | *—CH=C(Cl)—C(SO$_2$NH$_2$)=CH— |
| 42 | —C$_2$H$_5$ | —C$_2$H$_5$ | *—CH=C(Br)—C(SO$_2$NHCH$_3$)=CH— |
| 43 | do. | do. | *—CH=C(Cl)—C[SO$_2$N(CH$_3$)$_2$]=CH— |
| 44 | do. | do. | *—CH=C(OC$_2$H$_5$)—CH=CH— |
| 45 | do. | do. | *—C(SO$_2$NH$_2$)=CH—CH=CH— |
| 46 | do. | do. | *—C(SO$_2$NHCH$_3$)=CH—CH=CH— |
| 47 | do. | do. | *—C[SO$_2$N(CH$_3$)$_2$]=CH—CH=CH— |
| 48 | do. | do. | *—C[SO$_2$N(C$_2$H$_5$)$_2$]=CH—CH=CH— |
| 49 | do. | do. | *—CH=CH—C(CN)=CH— |
| 50 | do. | do. | *—CH=CH—C(CF$_3$)=CH— |
| 51 | do. | do. | *—C(CH$_3$)=CH—CH=C(Br)— |
| 52 | do. | do. | *—C(CN)=CH—CH=CH— |
| 53 | do. | —CH$_2$CH$_2$OCOC$_6$H$_5$ | *—CH=CH—CH=C(CF$_3$)— |
| 54 | do. | —C$_2$H$_5$ | *—CH=CH—CH=(OCH$_3$)— |
| 55 | do. | do. | *—CH=CH=CH=C(CN)— |
| 56 | —C$_2$H$_5$ | —C$_2$H$_5$ | *—N=CH—N=CH— |
| 57 | do. | do. | *—N=C(NHCOCH$_3$)—N=C(NHCOCH$_3$)— |
| 58 | do. | do. | *—CH=CH—N=CH— |
| 59 | do. | do. | *—C(SO$_2$NH$_2$)=CH—N=CH— |

The following dyestuffs too can be produced according to the directions given in the first Example, and their properties correspond generally to the products quoted previously.

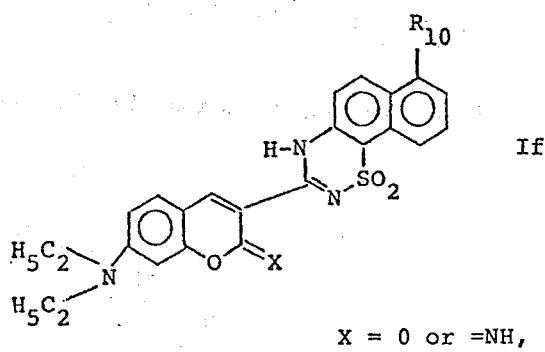

X = O or =NH,

Example 60   $R_{10}$ = H
Example 61   $R_{10}$ = —SO$_2$NH$_2$
Example 62   $R_{10}$ = —SO$_2$NHCH$_3$
Example 63   $R_{10}$ = —SO$_2$N(CH$_3$)$_2$.

APPLICATION EXAMPLE

7 Parts of the dyestuff produced according to Example 1 (formula Ie) are ground to a fine powder in a ball mill during 48 hours together with 4 parts dinaphthyl methane sodium disulphonate, 4 parts sodium cetyl sulphate and 5 parts anhydrous sodium sulphate.

1 Part of the dye preparation obtained in this way is mixed to a paste with a little water, and the resulting suspension is added through a sieve to a dye bath consisting of 3 parts sodium lauryl sulphate in 4000 parts water. The liquor ratio is 1 : 40. 100 Parts cleaned polyester fiber material are then put into the bath at 40° – 50° and 20 parts of an emulsified chlorinated benzole are added. The bath is heated slowly to 100° and dyeing is applied for 1 – 2 hours at 95° – 100°. The fibres are dyed a brilliant yellow with a greenish tinge. They are washed, soaped, washed again and dried. The level dyeing has good fastness to light, cross-dyeing, washing, water, sea water, perspiration, sublimation, flue gas, thermosetting, pleating and permanent pressing.

What is claimed is:

1. A compound of formula Ia,

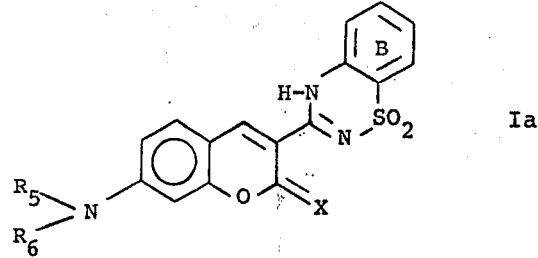

wherein

X is oxygen or NH, $R_5$ is alkyl which is unsubstituted or substituted by hydroxy, alkoxy, cyano, formyloxy, alkylcarbonyloxy, alkoxycarbonyloxy, alkoxycarbonyl, benzoyloxy, allyl or phenyl;

$R_6$ is hydrogen or one of the significances of $R_5$; and ring B is unsubstituted or substituted by chloro, bromo, methyl, alkoxy, cyano, thiocyano, trifluoromethyl, alkoxycarbonyl, benzyloxycarbonyl, alkylcarbonyloxy, acetylamino, propionylamino, benzoylamino, aminosulphonyl, alkylaminosulphonyl, dialkylaminosulphonyl, phenylaminosulphonyl or N-alkyl-N-phenylaminosulphonyl; and the alkyl and alkoxy named contain 1 to 4 carbon atoms.

2. A compound according to claim 1 of formula Ib,

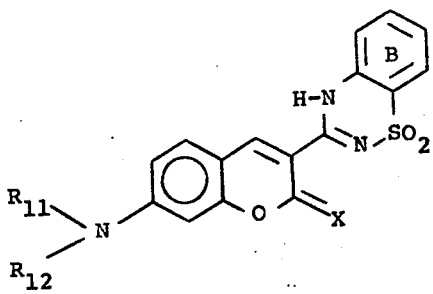

wherein
X is as defined in claim 1;
$R_{11}$ is ethyl which is unsubstituted or substituted by cyano, acetoxy, propionyloxy, methoxycarbonyl, ethoxycarbonyl, methoxycarbonyloxy or ethoxycarbonyloxy;
$R_{12}$ is allyl, phenyl or one of the significances of $R_{11}$; and
ring B is unsubstituted or substituted by chloro, bromo, methyl, methoxy, ethoxy, cyano, thiocyano, trifluoromethyl, methoxycarbonyl, ethoxycarbonyl, aminosulphonyl, methylaminosulphonyl or dimethylaminosulphonyl.

3. A compound according to claim 2 of formula Ic,

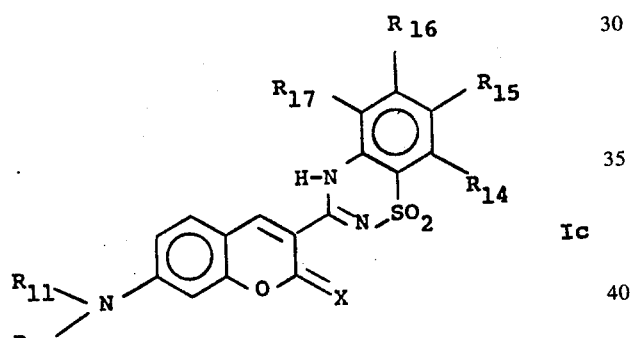

wherein
$R_{11}$, $R_{12}$ and X are as defined in claim 2;
$R_{14}$ and $R_{16}$ each, independently, are hydrogen, chloro, bromo, methyl, methoxy, cyano or trifluoromethyl;
$R_{15}$ is methoxycarbonyl, ethoxycarbonyl or one of the significances of $R_{14}$ and $R_{16}$; and
$R_{17}$ is aminosulphonyl, methylaminosulphonyl, dimethylaminosulphonyl or one of the significances or $R_{14}$ and $R_{16}$.

4. A compound according to claim 1 of the formula

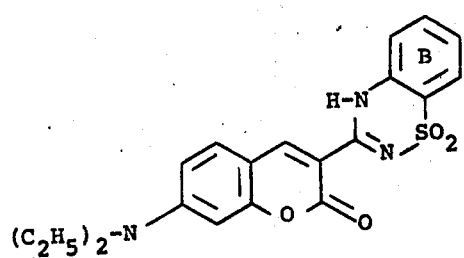

wherein ring B is unsubstituted or substituted by one or two substituents selected from methyl, chloro, trifluoromethyl and methoxy.

5. A compound according to claim 1 of the formula

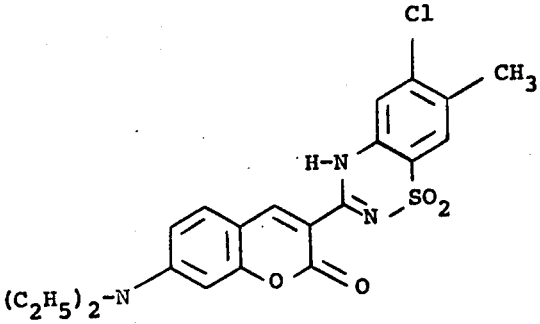

6. A compound according to claim 1 of the formula

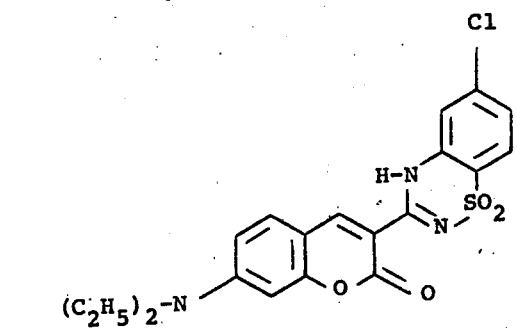

7. A compound according to claim 1 of the formula

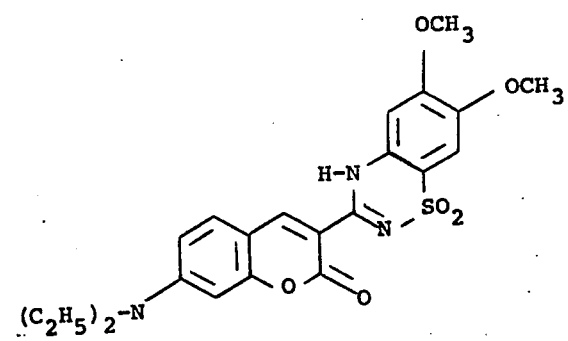

8. A compound according to claim 1 of the formula

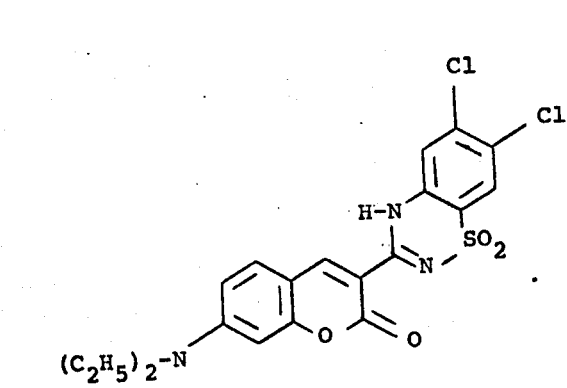

9. A compound according to claim 1 of the formula
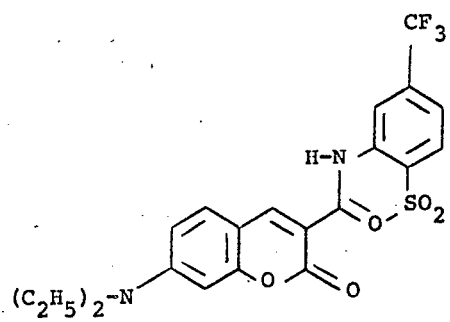
10. A compound according to claim 1 of the formula
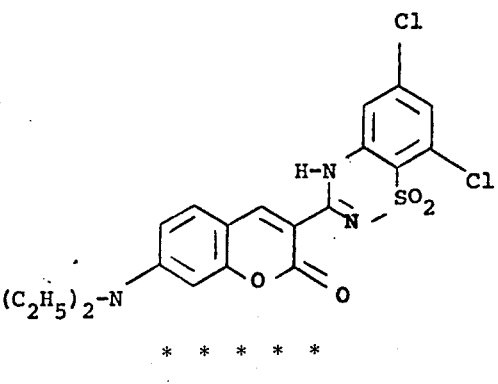
* * * * *